(12) United States Patent
Zinobile et al.

(10) Patent No.: US 8,207,377 B2
(45) Date of Patent: Jun. 26, 2012

(54) PROCESS FOR THE PRODUCTION OF ACETIC ACID

(75) Inventors: Raymond J. Zinobile, Houston, TX (US); Mark O. Scates, Houston, TX (US); Jonathan A. Makelki, Bay City, TX (US); Manuel Salado, Seabrook, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 12/959,085

(22) Filed: Dec. 2, 2010

(65) Prior Publication Data

US 2011/0077428 A1    Mar. 31, 2011

Related U.S. Application Data

(63) Continuation of application No. 11/116,771, filed on Apr. 28, 2005, now Pat. No. 7,855,306.

(51) Int. Cl.
*C07C 51/42* (2006.01)

(52) U.S. Cl. ................................................ 562/608

(58) Field of Classification Search ................ None
See application file for complete search history.

(56) References Cited

U.S. PATENT DOCUMENTS

| | | | |
|---|---|---|---|
| 3,769,329 A | 10/1973 | Paulik et al. | |
| 4,908,477 A | 3/1990 | Hartmann et al. | |
| 5,001,259 A | 3/1991 | Smith et al. | |
| 5,026,908 A | 6/1991 | Smith et al. | |
| 5,144,068 A | 9/1992 | Smith et al. | |
| 5,416,237 A | 5/1995 | Aubigne et al. | |
| 5,599,976 A | 2/1997 | Scates et al. | |
| 5,625,095 A | 4/1997 | Miura et al. | |
| 5,723,660 A | 3/1998 | Morimoto et al. | |
| 5,756,836 A | 5/1998 | Shimizu et al. | |
| 5,783,731 A | 7/1998 | Fisher et al. | |
| 5,916,422 A | 6/1999 | Kimura et al. | |
| 6,143,930 A | 11/2000 | Singh et al. | |
| 6,339,171 B1 | 1/2002 | Singh et al. | |
| 6,458,996 B1 | 10/2002 | Muskett | |
| 7,223,883 B2 | 5/2007 | Picard et al. | |
| 7,223,886 B2 | 5/2007 | Scates et al. | |
| 7,855,306 B2 * | 12/2010 | Zinobile et al. | 562/608 |
| 2006/0247466 A1 | 11/2006 | Zinoble et al. | |

FOREIGN PATENT DOCUMENTS

| | | |
|---|---|---|
| EP | 0161874 | 11/1985 |
| EP | 0487284 | 5/1992 |
| EP | 0497521 | 8/1992 |
| EP | 0687662 | 12/1995 |
| EP | 0768295 | 4/1997 |
| EP | 0976711 | 2/2000 |
| JP | 9-40590 | 2/1997 |
| WO | WO 98/17619 | 4/1998 |
| WO | WO 2004/033407 | 4/2004 |

OTHER PUBLICATIONS

Watson, Derrick, J., "The Cativa™ Process for the Production of Acetic Acid", Catalysis of Organic Reactions, pp. 369-380 (1998).
R.T. Eby & T.C. Singleton, Methanol Carbonylation to Acetic Acid, Applied Industrial Catalysis, vol. 1, pp. 275-296 (1983).
"Handbook of Chemistry and Physics", CRC Press, Cleveland, Ohio, Mar. 2002 (83 edition).

* cited by examiner

*Primary Examiner* — Paul A Zucker

(57) ABSTRACT

A process for the reduction and/or removal of permanganate reducing compounds formed by the carbonylation of methanol in the presence of a Group VIII metal carbonylation catalyst to produce acetic acid is disclosed. More specifically, a process for reducing and/or removing permanganate reducing compounds or their precursors from intermediate streams during the formation of acetic acid by said carbonylation processes is disclosed. In particular, a process in which a low boiling overhead vapor stream from a light ends column is subjected to a single distillation to obtain an overhead that is subjected to an extraction to selectively remove and/or reduce PRC's from the process is disclosed.

31 Claims, 1 Drawing Sheet

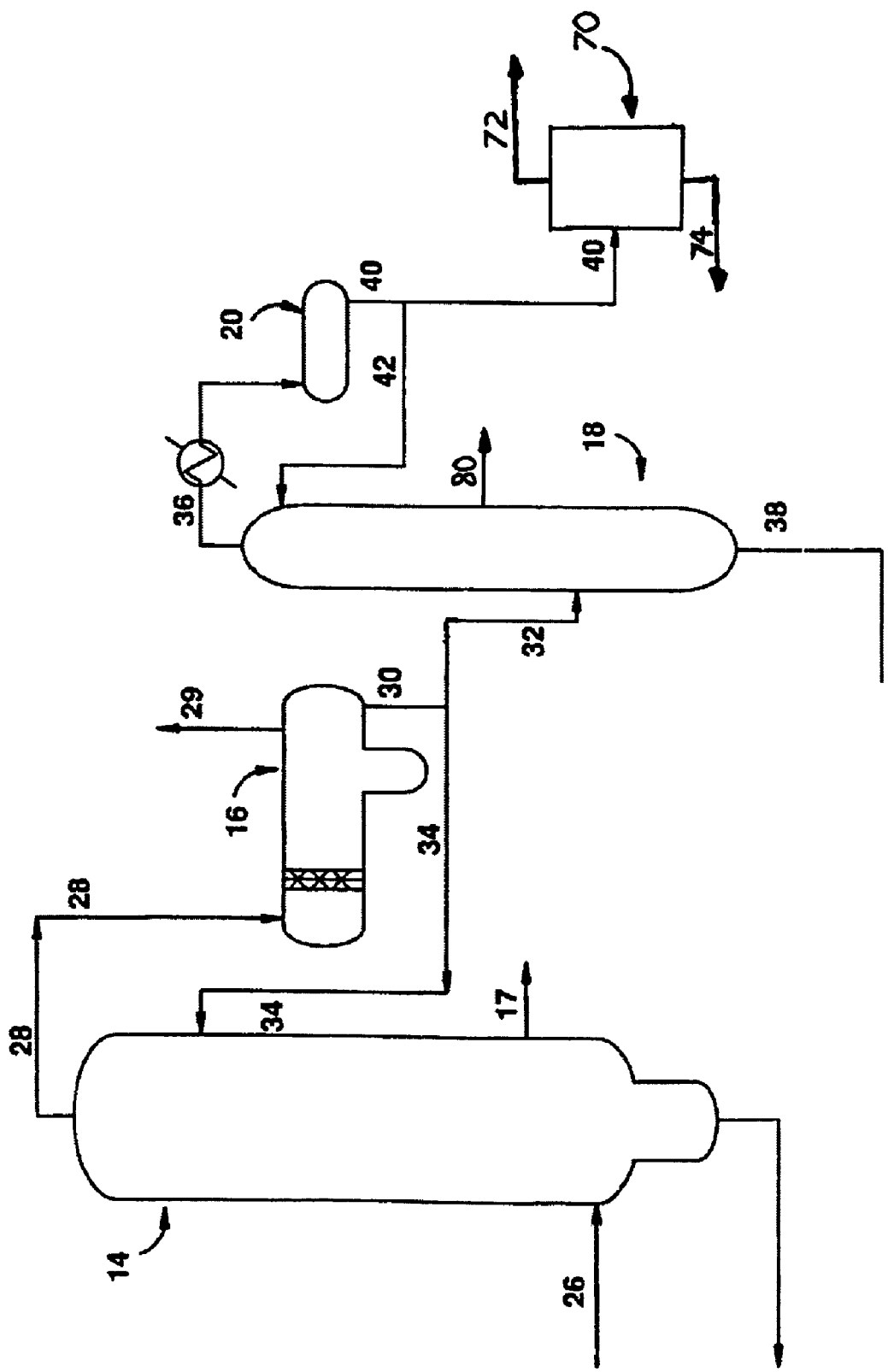

PROCESS FOR THE PRODUCTION OF ACETIC ACID

This application is a continuation of U.S. application Ser. No. 11/116,771, filed on Apr. 28, 2005, the entire content and disclosure of which is hereby incorporated by reference.

BACKGROUND OF THE INVENTION

1. Field of the Invention

This invention relates to a process for the production of acetic acid and, in particular, to an improved process for the reduction and/or removal of permanganate reducing compounds formed by the carbonylation of methanol in the presence of a Group VIII metal carbonylation catalyst to produce acetic acid. More specifically, this invention relates to an improved process for reducing and/or removing permanganate reducing compounds or their precursors from intermediate streams during the formation of acetic acid by said carbonylation processes.

2. Technical Background

Among currently employed processes for synthesizing acetic acid, one of the most useful commercially is the catalyzed carbonylation of methanol with carbon monoxide as taught in U.S. Pat. No. 3,769,329, issued to Paulik et al. on Oct. 30, 1973. The carbonylation catalyst contains rhodium, either dissolved or otherwise dispersed in a liquid reaction medium or supported on an inert solid, along with a halogen-containing catalyst promoter as exemplified by methyl iodide. The rhodium can be introduced into the reaction system in any of many forms. Likewise, the nature of the halide promoter is not generally critical. The patentees disclose a very large number of suitable promoters, most of which are organic iodides. Most typically and usefully, the reaction is conducted by continuously bubbling carbon monoxide gas through a liquid reaction medium in which the catalyst is dissolved.

An improvement in the prior art process for the carbonylation of an alcohol to produce the carboxylic acid having one carbon atom more than the alcohol in the presence of a rhodium catalyst is disclosed in commonly assigned U.S. Pat. Nos. 5,001,259, issued Mar. 19, 1991; 5,026,908, issued Jun. 25, 1991; and 5,144,068, issued Sep. 1, 1992; and European Patent No. EP 0 161 874 B2, published Jul. 1, 1992. As disclosed therein, acetic acid is produced from methanol in a reaction medium containing methyl acetate, methyl halide, especially methyl iodide, and rhodium present in a catalytically effective concentration. These patents disclose that catalyst stability and the productivity of the carbonylation reactor can be maintained at surprisingly high levels, even at very low water concentrations, i.e., 4 weight percent or less, in the reaction medium (despite the general industrial practice of maintaining approximately 14-15 wt % water) by maintaining in the reaction medium, along with a catalytically effective amount of rhodium and at least a finite concentration of water, a specified concentration of iodide ions over and above the iodide ion that is present as hydrogen iodide. This iodide ion is a simple salt, with lithium iodide being preferred. The patents teach that the concentration of methyl acetate and iodide salts are significant parameters in affecting the rate of carbonylation of methanol to produce acetic acid, especially at low reactor water concentrations. By using relatively high concentrations of the methyl acetate and iodide salt, one obtains a surprising degree of catalyst stability and reactor productivity even when the liquid reaction medium contains water in concentrations as low as about 0.1 wt %, so low that it can broadly be defined simply as "a finite concentration" of water. Furthermore, the reaction medium employed improves the stability of the rhodium catalyst, i.e., resistance to catalyst precipitation, especially during the product recovery steps of the process. In these steps, distillation for the purpose of recovering the acetic acid product tends to remove from the catalyst the carbon monoxide, which in the environment maintained in the reaction vessel, is a ligand with stabilizing effect on the rhodium. U.S. Pat. Nos. 5,001,259, 5,026,908 and 5,144,068 are herein incorporated by reference.

It has been found that although a low water carbonylation process for producing acetic acid reduces such by-products as carbon dioxide, hydrogen, and propionic acid, the amount of other impurities, present generally in trace amounts, can be increased by a low water carbonylation process, and the quality of acetic acid sometimes suffers when attempts are made to increase the production rate by improving catalysts, or modifying reaction conditions.

These trace impurities affect quality of acetic acid, especially when they are recirculated through the reaction process, which, among other things, can result in the build up over time of these impurities. The impurities that decrease the permanganate time of the acetic acid, a quality test commonly used in the acetic acid industry, include carbonyl compounds and unsaturated carbonyl compounds. As used herein, the phrase "carbonyl" is intended to mean compounds that contain aldehyde or ketone functional groups, which compounds may or may not possess unsaturation. See *Catalysis of Organic Reaction,* 75, 369-380 (1998), for further discussion on impurities in a carbonylation process.

The present invention is directed to reducing and/or removing permanganate reducing compounds (PRC's) such as acetaldehyde, acetone, methyl ethyl ketone, butyraldehyde, crotonaldehyde, 2-ethyl crotonaldehyde, and 2-ethyl butyraldehyde and the like, and the aldol condensation products thereof. The present invention may also lead to reduction of propionic acid.

The carbonyl impurities described above, such as acetaldehyde, may react with iodide catalyst promoters to form multi-carbon alkyl iodides, e.g., ethyl iodide, propyl iodide, butyl iodide, pentyl iodide, hexyl iodide, and the like. It is desirable to remove multi-carbon alkyl iodides from the reaction product because even small amounts of these impurities in the acetic acid product tend to poison the catalyst used in the production of vinyl acetate, a product commonly produced from acetic acid. Thus, the present invention may also lead to reduction or removal of multi-carbon alkyl iodides, in particular $C_{2-12}$ alkyl iodide compounds. Accordingly, because many impurities originate with acetaldehyde, it is a primary objective to remove carbonyl impurities, notably acetaldehyde, from the process so as to reduce the multi-carbon alkyl iodide content.

Conventional techniques to remove such impurities include treating the acetic acid product streams with oxidizers, ozone, water, methanol, activated-carbon, amines, and the like. Such treatments may or may not be combined with distillation of the acetic acid. The most typical purification treatment involves a series of distillations of the final product. It is also known to remove carbonyl impurities from organic streams by treating the organic streams with an amine compound such as hydroxylamine, which reacts with the carbonyl compounds to form oximes, followed by distillation to separate the purified organic product from the oxime reaction products. However, the additional treatment of the final product adds cost to the process, and distillation of the treated acetic acid product can result in additional impurities being formed.

While it is possible to obtain acetic acid of relatively high purity, the acetic acid product formed by the low-water carbonylation process and purification treatment described above frequently remains somewhat deficient with respect to the permanganate time due to the presence of small proportions of residual impurities. Because a sufficient permanganate time is an important commercial test, which the acid product may be required to meet to be suitable for many uses, the presence of impurities that decrease permanganate time is objectionable. Moreover, it has not been economically or commercially feasible to remove minute quantities of these impurities from the acetic acid by distillation because some of the impurities have boiling points close to that of the acetic acid product or halogen-containing catalyst promoters, such as methyl iodide.

It has thus become important to identify economically viable methods of removing impurities elsewhere in the carbonylation process without contaminating the final product or adding unnecessary costs. For example, a method for manufacturing high purity acetic acid by adjusting the acetaldehyde concentration of the reaction solution below a certain amount, such as 1500 ppm, has been disclosed. It is stated that by maintaining the acetaldehyde concentration below this threshold, it is possible to suppress the formation of impurities such that one need only distill the crude acetic acid product to obtain high purity acetic acid.

The art has also disclosed that carbonyl impurities present in the acetic acid product streams generally concentrate in the overhead from the light ends column. Accordingly, the light ends column overhead has been treated with an amine compound (such as hydroxylamine), which reacts with the carbonyl compounds to form oxime derivatives that can be separated from the remaining overhead by distillation, resulting in an acetic acid product with improved permanganate time.

Other processes have been described for producing high purity acetic acid in which it is stated that an acetaldehyde concentration of 400 ppm or less is maintained in the reactor by using distillation to remove acetaldehyde. Streams suggested for processing to remove acetaldehyde include a light phase containing primarily water, acetic acid and methyl acetate; a heavy phase containing primarily methyl iodide, methyl acetate and acetic acid; an overhead stream containing primarily methyl iodide and methyl acetate; or a recirculating stream formed by combining the light and heavy phase.

It has been disclosed in commonly assigned U.S. Pat. Nos. 6,143,930 and 6,339,171 that it is possible to significantly reduce the undesirable impurities in the acetic acid product by performing a multi-stage purification on the light ends column overhead. These patents disclose a purification process in which the light ends overhead is distilled twice, in each case taking the acetaldehyde overhead and returning a methyl iodide rich residuum to the reactor. The acetaldehyde-rich distillate obtained after the two distillation steps is optionally extracted with water to remove the majority of the acetaldehyde for disposal, leaving a significantly lower acetaldehyde concentration in the raffinate that is recycled to the reactor. U.S. Pat. Nos. 6,143,930 and 6,339,171 are incorporated herein by reference in their entirety.

While the above-described processes have been successful in removing carbonyl impurities from the carbonylation system and for the most part controlling acetaldehyde levels and permanganate time problems in the final acetic acid product, further improvements can still be made. Accordingly, there remains a need for alternative processes to improve the efficiency of acetaldehyde removal. The present invention provides one such alternative solution.

SUMMARY OF THE INVENTION

This invention relates to a process for the production of acetic acid and, in particular, an improved process for the reduction and/or removal of permanganate reducing compounds and alkyl iodides formed by the carbonylation of methanol in the presence of a Group VIII metal carbonylation catalyst to produce acetic acid. More specifically, this invention relates to an improved process for reducing and/or removing permanganate reducing compounds or their precursors from intermediate streams during the formation of acetic acid by said carbonylation processes.

In one aspect, the present invention provides a process for the reduction and/or removal of permanganate reducing compounds (PRC's) formed in the carbonylation of a carbonylatable reactant to produce a carbonylation product comprising acetic acid. The process comprises the steps of: (a) separating the carbonylation product to provide a vapor overhead stream comprising acetic acid and a less volatile catalyst phase; (b) distilling the vapor overhead stream to yield a purified acetic acid product and a low boiling overhead vapor stream comprising methyl iodide, water, acetic acid, methyl acetate, and at least one PRC; (c) condensing the low boiling overhead vapor stream and biphasically separating it to form a condensed heavy liquid phase and a condensed light liquid phase; (d) distilling the condensed light liquid phase in a single distillation column to form a second vapor phase stream overhead and a higher boiling liquid phase residuum, wherein the second vapor phase stream is enriched with PRC's with respect to the condensed light liquid phase; and (e) condensing the second vapor phase stream and extracting the condensed stream with water to obtain an aqueous acetaldehyde stream comprising PRC and a raffinate comprising methyl iodide. In certain variations, the process can be operated with or without a sidestream comprising methyl acetate being taken from the distillation column of step (d).

In another aspect, the present invention provides a process for the reduction and/or removal of permanganate reducing compounds (PRC's) formed in the carbonylation of a carbonylatable reactant to produce a carbonylation product comprising acetic acid, comprising the steps of: (a) separating the carbonylation product to provide a vapor overhead stream comprising acetic acid and a less volatile catalyst phase; (b) distilling the vapor overhead stream to yield a purified acetic acid product and a low boiling overhead vapor stream comprising methyl iodide, water, acetic acid, methyl acetate, and at least one PRC; (c) condensing the low boiling overhead vapor stream and biphasically separating it to form a condensed heavy liquid phase and a condensed light liquid phase; (d) distilling the condensed light liquid phase in a single distillation column to form a second vapor phase stream overhead and a higher boiling liquid phase residuum, wherein the second vapor phase stream is enriched with PRC's with respect to the condensed light liquid phase and wherein the higher boiling liquid phase residuum is enriched with methyl acetate with respect to said second vapor phase stream overhead; and (e) condensing the second vapor phase stream and extracting the condensed stream with water to obtain an aqueous acetaldehyde stream comprising PRC and a raffinate comprising methyl iodide. In certain variations, the process can be operated with or without a sidestream comprising methyl acetate being taken from the distillation column of step (d)

In a third aspect, the present invention provides a process for the reduction and/or removal of permanganate reducing compounds (PRC's) formed in the carbonylation of a carbonylatable reactant to produce a carbonylation product comprising acetic acid, comprising the steps of: (a) separating the carbonylation product to provide a vapor overhead stream comprising acetic acid and a less volatile catalyst phase; (b) distilling the vapor overhead stream to yield a purified acetic acid product and a low boiling overhead vapor stream comprising methyl iodide, water, acetic acid, methyl acetate, and at least one PRC; (c) condensing the low boiling overhead vapor stream and biphasically separating it to form a condensed heavy liquid phase and a condensed light liquid phase; (d) distilling the condensed light liquid phase in a single distillation column to form a second vapor phase stream overhead and a higher boiling liquid phase residuum, wherein the second vapor phase stream is enriched with PRC's with respect to the condensed light liquid phase; (e) removing a sidestream comprising methyl acetate from the distillation column of step (d), wherein the higher boiling liquid phase residuum and the sidestream are cumulatively enriched with methyl acetate with respect to said second vapor phase stream; and (f) condensing the second vapor phase stream and extracting the condensed stream with water to obtain an aqueous acetaldehyde stream comprising PRC and a raffinate comprising methyl iodide.

BRIEF DESCRIPTION OF THE DRAWINGS

FIG. 1 illustrates various embodiments of the present invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is intended to cover all modifications, equivalents and alternatives falling within the scope of the invention as defined by the appended claims.

DESCRIPTION OF ILLUSTRATIVE EMBODIMENTS

This invention relates to a process for the production of acetic acid and, in particular, an improved process for the reduction and/or removal of permanganate reducing compounds formed by the carbonylation of methanol in the presence of a Group VIII metal carbonylation catalyst to produce acetic acid. More specifically, this invention relates to an improved process for reducing and/or removing permanganate reducing compounds or their precursors from intermediate streams during the formation of acetic acid by said carbonylation processes.

In particular, the present invention relates to a process in which a condensed light phase from a light ends column overhead is subjected to a single distillation to obtain an overhead that is subjected to an extraction to selectively reduce and/or remove PRC's from the process. Among other advantages, the present invention is able to reduce and/or remove PRC's from the process using a single distillation column and extraction combination as compared to previous process that utilized more than one distillation column with (or without) extraction to reduce and/or remove PRC's from a condensed light phase from a light ends column overhead. Additional advantages include, but are not limited to, lower energy usage and reduced equipment and associated costs.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The purification process of the present invention is useful in any process used to carbonylate methanol (or another carbonylatable reactant, including, but not limited to, methyl acetate, methyl formate or dimethyl ether, or mixtures thereof) to acetic acid in the presence of a Group VIII metal catalyst, such as rhodium, and a halogen-containing catalyst promoter. A particularly useful process is the low water rhodium-catalyzed carbonylation of methanol to acetic acid as exemplified in U.S. Pat. No. 5,001,259.

Generally, the rhodium component of the catalyst system is believed to be present in the form of a coordination compound of rhodium with a halogen component providing at least one of the ligands of such coordination compound. In addition to the coordination of rhodium and halogen, it is also believed that carbon monoxide will coordinate with rhodium. The rhodium component of the catalyst system may be provided by introducing into the reaction zone rhodium in the form of rhodium metal, rhodium salts such as the oxides, acetates, iodides, carbonates, hydroxides, chlorides, etc., or other compounds that result in the formation of a coordination compound of rhodium in the reaction environment.

The halogen-containing catalyst promoter of the catalyst system consists of a halogen compound comprising an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter will include methyl halide, and more preferably methyl iodide.

The liquid reaction medium employed may include any solvent compatible with the catalyst system and may include pure alcohols, or mixtures of the alcohol feedstock and/or the desired carboxylic acid and/or esters of these two compounds. A preferred solvent and liquid reaction medium for the low water carbonylation process contains the desired carboxylic acid product. Thus, in the carbonylation of methanol to acetic acid, a preferred solvent system contains acetic acid.

Water is contained in the reaction medium but desirably at concentrations well below that which has heretofore been thought practical for achieving sufficient reaction rates. It has previously been taught, e.g., U.S. Pat. No. 3,769,329, that in rhodium-catalyzed carbonylation reactions of the type set forth in this invention, the addition of water exerts a beneficial effect upon the reaction rate. Thus, commercial operations are commonly run at water concentrations of at least about 14 wt %. Accordingly, it has been quite unexpected that reaction rates substantially equal to and above reaction rates obtained with such comparatively high levels of water concentration can be achieved with water concentrations below 14 wt % and as low as about 0.1 wt %.

In accordance with the carbonylation process most useful to manufacture acetic acid according to the present invention, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide being preferred. It has been found, e.g., U.S. Pat. No. 5,001,259, that under low water concentrations, methyl acetate and lithium iodide act as rate promoters only when relatively high concentrations of each of these components are present and that the promotion is higher when both of these components are present simultaneously. The concentration of iodide ion maintained in the reaction medium of the preferred carbonylation reaction system is believed to be quite high as compared with what little prior art there is dealing with the use of halide salts in reaction systems of this sort. The absolute concentration of iodide ion content is not a limitation on the usefulness of the present invention.

The carbonylation reaction of methanol to acetic acid product may be carried out by contacting the methanol feed with gaseous carbon monoxide bubbled through a acetic acid solvent reaction medium containing the rhodium catalyst, methyl iodide promoter, methyl acetate, and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or quaternary cation such as a quaternary amine or phosphine or inorganic cation can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable. In the low water carbonylation process most useful in this invention, the additional iodide ion over and above the iodide ion present as hydrogen iodide is generally present in the catalyst solution in amounts such that the total iodide ion concentration is from about 2 to about 20 wt % and the methyl acetate is generally present in amounts of from about 0.5 to about 30 wt %, and the methyl iodide is generally present in amounts of from about 5 to about 20 wt %. The rhodium catalyst is generally present in amounts of from about 200 to about 2000 parts per million (ppm).

Typical reaction temperatures for carbonylation will be from about 150 to about 250° C., with the temperature range of about 180 to about 220° C. being a preferred range. The carbon monoxide partial pressure in the reactor can vary widely but is typically about 2 to about 30 atmospheres, and preferably, about 3 to about 10 atmospheres. Because of the partial pressure of by-products and the vapor pressure of the contained liquids, the total reactor pressure will range from about 15 to about 40 atmospheres.

A typical reaction and acetic acid recovery system that is used for the iodide-promoted rhodium catalyzed carbonylation of methanol to acetic acid in accordance with the present invention is shown in FIG. 1 and includes a liquid phase carbonylation reactor, flasher, and a methyl iodide acetic acid light ends column ("light ends column") 14. In the process, carbonylation product obtained in the reactor is provided to the flasher where a volatile ("vapor") overhead stream comprising acetic acid and a less volatile catalyst phase (catalyst-containing solution) are obtained. The volatile overhead stream comprising acetic acid is provided by stream 26 to the light ends column 14 where distillation yields a purified acetic acid product that is removed via sidestream 17 and an overhead distillate stream 28 (hereafter "low-boiling overhead vapor stream"). Acetic acid removed via sidestream 17 can be subjected to further purification, such as to a drying column for selective separation of acetic acid from water.

The reactor and flasher are not shown in FIG. 1. These are considered standard equipment now well known in the carbonylation process art. The carbonylation reactor is typically either a stirred vessel or bubble-column type within which the reacting liquid or slurry contents are maintained automatically at a constant level. Into this reactor, there are continuously introduced fresh methanol, carbon monoxide, sufficient water as needed to maintain at least a finite concentration of water in the reaction medium. Also introduced into the reactor is a recycled catalyst solution, such as from the flasher base, a recycled methyl iodide phase, a recycled methyl acetate phase, and a recycled aqueous acetic acid phase. A recycled phase may contain one or more of the foregoing components.

Distillation systems are employed that provide means for recovering the crude acetic acid and recycling catalyst solution, methyl iodide, methyl acetate, and other system components within the process. In a typical carbonylation process, carbon monoxide is continuously introduced into the carbonylation reactor, desirably below the agitator, which is used to stir the contents. The gaseous feed is thoroughly dispersed through the reacting liquid by this stirring means. A gaseous purge stream is desirably vented from the reactor to prevent buildup of gaseous by-products and to maintain a set carbon monoxide partial pressure at a given total reactor pressure. The temperature of the reactor is controlled and the carbon monoxide feed is introduced at a rate sufficient to maintain the desired total reactor pressure.

Liquid product is drawn off from the carbonylation reactor at a rate sufficient to maintain a constant level therein and is introduced to the flasher. In the flasher, a catalyst-containing solution (catalyst phase) is withdrawn as a base stream (predominantly acetic acid containing the rhodium and the iodide salt along with lesser quantities of methyl acetate, methyl iodide, and water), while a vapor overhead stream comprising acetic acid is withdrawn overhead. The vapor overhead stream comprising acetic acid also contains methyl iodide, methyl acetate, and water. Dissolved gases exiting the reactor and entering the flasher comprise a portion of the carbon monoxide and may also contain gaseous by-products such as methane, hydrogen, and carbon dioxide. Such dissolved gases exit the flasher as part of the overhead stream. The overhead stream is directed to the light ends column 14 as stream 26.

It has been disclosed in U.S. Pat. Nos. 6,143,930 and 6,339,171 that there is generally a higher concentration of the PRC's and in particular acetaldehyde content in the low-boiling overhead vapor stream 28 exiting column 14 than in the high-boiling residue stream exiting column 14. Thus, in accordance with the present invention, low-boiling overhead vapor stream 28, containing PRC's is subjected to additional processing to reduce and/or remove the amount of PRC's present. Low-boiling overhead vapor stream 28, therefore, is condensed and directed to an overhead receiver decanter 16. In addition to PRC's, low-boiling overhead vapor stream 28 will typically contain methyl iodide, methyl acetate, acetic acid, and water. Conditions are desirably maintained in the process such that low-boiling overhead vapor stream 28, once in decanter 16, will separate into a light phase and a heavy phase. Generally, low-boiling overhead vapor stream 28 is chilled to a temperature sufficient to condense and separate the condensable methyl iodide, methyl acetate, acetaldehyde and other carbonyl components, and water into two phases. A portion of stream 28 may include noncondensable gases such as carbon dioxide, hydrogen, and the like that can be vented as shown in stream 29 on FIG. 1.

The condensed light phase in decanter 16 will generally comprise water, acetic acid, and PRC's, as well as quantities of methyl iodide and methyl acetate. The condensed heavy phase in decanter 16 will generally comprise methyl iodide, methyl acetate, and PRC's.

The present invention may broadly be considered as an improved process for distilling PRC's, primarily aldehydes such as acetaldehyde, from a low-boiling overhead vapor stream, particularly the condensed light phase of a low-boiling overhead vapor stream 28 from a light ends distillation column 14. In accordance with the present invention, a condensed light phase of a low-boiling overhead vapor stream 28 from a light ends distillation column 14 is distilled once and then subjected to single- or multi-stage extraction to reduce and/or remove PRC's.

This process, such as that in the embodiments disclosed in FIG. 1, is distinct from prior processes, such as that disclosed in U.S. Pat. No. 6,339,171, including that illustrated in FIG. 1 of U.S. Pat. No. 6,339,171.

In accordance with the present invention, disclosed in FIG. 1, the low-boiling overhead vapor stream 28 contains methyl iodide, methyl acetate, PRC's such as acetaldehyde and optionally other carbonyl components. The low-boiling overhead vapor stream 28 also contains water and some quantity of acetic acid.

The low-boiling overhead vapor stream 28 is then condensed and separated (in vessel 16) to form a condensed heavy liquid phase containing the larger proportion of methyl iodide, but also containing PRC's, and a condensed light liquid phase (taken of as stream 30), notably containing PRC's, water, and acetic acid but also generally containing some quantity of both methyl iodide and methyl acetate.

While either phase of the light ends overhead, i.e., low-boiling overhead vapor stream 28, may be subsequently processed to remove the PRC's and primarily the acetaldehyde component of the stream, in the present invention, the PRC's are removed from the condensed light liquid phase 30.

Thus, the condensed heavy liquid phase in the decanter 16 can be conveniently recirculated, either directly or indirectly, to the reactor (not shown in FIG. 1). For example, a portion of this condensed heavy liquid phase can be recirculated to the reactor, with a slip stream, generally a small amount, e.g., 25 vol. %, preferably less than about 20 vol. %, of the heavy liquid phase being directed to a carbonyl treatment process. This slip stream of the heavy liquid phase may be treated individually or may be combined with the condensed light liquid phase 30 for further distillation and extraction of carbonyl impurities in accordance with the present invention.

In accordance with the present invention, condensed light liquid phase 30 is directed to distillation column 18, which serves to form a second vapor phase 36 enriched in PRC's, notably acetaldehyde, but also containing methyl iodide due to the similar boiling points of methyl iodide and acetaldehyde. Second vapor phase 36 is condensed and then extracted with water to reduce and/or remove PRC's, notably acetaldehyde. In a preferred embodiment a portion of the condensed stream 36 is provided as reflux to distillation column 18. This can be accomplished, as shown in FIG. 1, by provided the condensed stream 36 to an overhead receiver 20, from which a portion of condensed stream 36 can be provided to the extraction step (generally indicated as 70) by stream 40 and another portion of condensed stream 36 can be provided as reflux to distillation column 18 by stream 42.

Acetaldehyde is extracted by water to obtain an aqueous acetaldehyde stream 72, which will generally be treated as a waste. The raffinate from the extraction, notably containing methyl iodide is desirably returned to the carbonylation process by stream 74. In various embodiments, aqueous acetaldehyde stream 72 can be stripped of aldehyde for treatment as waste with water being recirculated for use in the process, such as for the water used in extraction 70.

In the present invention, a primary concern is in the extraction step that separates acetaldehyde from methyl iodide. The efficiency of this separation is primarily affected by the relative solubility of acetaldehyde and methyl iodide in water. While acetaldehyde is miscible in water, methyl iodide is not. However, the solubility of methyl iodide in water increases, with a concomitant loss of methyl iodide from the process system, with increasing levels of methyl acetate and/or methanol. At high enough methyl acetate and/or methanol levels, phase separation of methyl iodide in the water extraction may not occur. Similarly, phase separation of methyl iodide in the water extraction may not occur if acetic acid concentrations are sufficiently high. Thus, it is desirable that the distillate that is condensed and provided for extraction contain methanol and methyl acetate at a combined concentration of less than about 10 wt. %, more desirably less than about 5 wt. %, even more desirably less than about 2 wt. %, and even more desirably less than about 1.5 wt. %. It is desirable that the distillate that is condensed and provided for extraction contain less than about 3 wt. % acetic acid, more desirably less than about 1 wt. %, and even more desirably less than about 0.5 wt. %. Particularly desired would be acetic acid concentrations approaching zero wt. %.

Thus, in the process of the present invention, a single distillation is conducted in distillation column 18 under conditions designed to control, notably minimize, the quantities of methyl acetate and acetic acid in second vapor phase stream 36. Desirably, minimization of quantities of methyl acetate and acetic acid in second vapor phase stream 36 is achieved while simultaneously maintaining higher acetaldehyde levels in second vapor phase stream 36 than in the residuum of distillation column 18. It is desirable that the residuum of distillation column 18 contain less than about 0.3 wt. % acetaldehyde, more desirably less than about 0.2 wt. %, and even more desirably less than about 0.1 wt. %. Particularly desired would be acetaldehyde concentrations approaching zero wt. %.

In prior art processes, such as that illustrated in FIG. 1 of U.S. Pat. No. 6,339,171, two distillation steps are conducted in order to obtain a final vapor distillate containing sufficiently low quantities of methyl acetate, methanol, and acetic acid such that the distillate can be subjected to extraction with water to selectively separate acetaldehyde from methyl iodide. In such prior art processes, water and acetic acid are preferentially separated as a residuum in the first column with methyl acetate in the distillate. Subsequently, methyl acetate is preferentially separated as a residuum in the second column. The prior art did not teach that methyl acetate, acetic acid, and water could be effectively removed as residuum using a single distillation column without having an undesirable concentration of acetaldehyde in the residuum. Similarly, the prior art did not teach that acetaldehyde could be effectively concentrated in the distillate of a single column without obtaining an undesirable concentration of methyl acetate in the distillate. As a result of their efforts, the present inventors have found that such separations can be achieved using a single distillation step, resulting in improved process efficiency.

Thus, in accordance with one embodiment of the present invention, illustrated in FIG. 1, low-boiling overhead vapor stream 28 is condensed in overhead receiver decanter 16 where it is biphasically separated to form a condensed heavy liquid phase and a light condensed liquid phase 30. The light condensed liquid phase 30 is provided to distillation column 18 via stream 30/32. In this and other embodiments of the present invention, a portion of stream 30 can be directed back to the light ends column 14 as reflux stream 34.

In distillation column 18, a second vapor phase stream 36 overhead and a higher boiling liquid phase residuum stream 38 are formed. The second vapor phase stream 36 overhead is enriched with PRC, notably acetaldehyde, with respect to the light condensed liquid phase 30. The second vapor phase stream 36 overhead is deficient with methyl acetate, methanol, and/or acetic acid (desirably all three) with respect to said light condensed liquid phase 30. The higher boiling liquid phase residuum stream 38 is enriched with methyl acetate, methanol, and/or acetic acid (desirably all three) with respect to said second vapor phase stream 36. Desirably, the second vapor phase stream 36 overhead is enriched with PRC, notably acetaldehyde, with respect to the higher boiling liquid phase residuum stream 38. The higher boiling liquid phase residuum stream 38 can be, and preferably is, retained in the process.

One of ordinary skill in the art having the benefit of this disclosure can design and operate a distillation column to achieve the desired results of the present invention. Such efforts, although possibly time-consuming and complex, would nevertheless be routine for one of ordinary skill in the art having the benefit of this disclosure. Accordingly, the practice of this invention is not necessarily limited to specific characteristic of a particular distillation column or the operation characteristics thereof, such as the total number of stages, the feed point, reflux ratio, feed temperature, reflux temperature, column temperature profile, and the like.

Further in accordance with this first embodiment of the present invention, second vapor phase stream 36 is extracted with water (generally indicated by 70) to remove and/or reduce PRC's, notably acetaldehyde. Acetaldehyde is extracted by the water to obtain aqueous acetaldehyde stream 72, which is PRC-rich, and in particular acetaldehyde-rich. Aqueous acetaldehyde stream 72 will generally be treated as a waste, although in some embodiments acetaldehyde may be stripped, with the water being recirculated to the process. The raffinate, notably containing methyl iodide is desirably returned to the carbonylation process by stream 74. The efficiency of the extraction will depend on such things as the number of extraction stages and the water to feed ratio.

Extraction with water 70, in accordance with this first or other embodiments of the present invention, can be either a singlestage or multistage extraction and any equipment used to conduct such extractions can be used in the practice of the present invention. Multistage extraction is preferred. For example, extraction 70 can be accomplished by combining stream 40 with water and providing the combination successively to a mixer and then a separator. Multiple such combinations of mixer and separator can be operated in series to obtain a multistage extraction. Optionally, and desirably, multistage extraction is accomplished in a single vessel having a series of trays. The vessel may be equipped with paddle(s) or other mechanisms for agitation to increase extraction efficiency. In such a multistage extraction vessel, stream 40 is desirably provided proximate to one end of the vessel with water being provided proximate to the other end of the vessel or such other location to obtain a countercurrent flow.

The mutual solubility between the two phases in the extraction can increase with temperature. Accordingly, it is desirable that the extraction be conducted at a combination of temperature and pressure such that the extractor contents can be maintained in the liquid state. Moreover, it is desirable to minimize the temperatures to which stream 40 is exposed to minimize the likelihood of polymerization and condensation reactions involving acetaldehyde. Water used in the extraction 70 is desirably from an internal stream so as to maintain water balance within the reaction system. Dimethyl ether (DME) can be introduced to the extraction to improve the separation of methyl iodide in the extraction, i.e., to reduce the loss of methyl iodide into the aqueous acetaldehyde stream 72. The DME can be introduced to the process or formed in situ.

In accordance with a second embodiment of the present invention, also illustrated in FIG. 1, low-boiling overhead vapor stream 28 is condensed in decanter 16 where it is biphasically separated to form a condensed heavy liquid phase and a condensed light liquid phase 30. The condensed light liquid phase 30 is provided to distillation column 18 via stream 30/32. Again, in this and other embodiments of the present invention, a portion of stream 30 can be directed back to the light ends column 14 as reflux stream 34. In distillation column 18, a second vapor phase stream 36 overhead and a higher boiling liquid phase residuum stream 38 are formed. A sidestream 80, comprising methyl acetate, is also taken.

The sidestream 80 allows the distillation column 18 to be operated under conditions desirable for obtaining a higher concentration of acetaldehyde in second vapor phase stream 36 while providing a mechanism for removing methyl acetate that might otherwise build up in the center of distillation column 18 or be pushed into the second vapor phase stream 36 overhead. The sidestream 80, comprising methyl acetate, is preferably retained in the process.

In this second embodiment, the second vapor phase stream 36 overhead is enriched with PRC, notably acetaldehyde, with respect to light condensed liquid phase 30. The second vapor phase stream 36 overhead is deficient with methyl acetate, methanol, and/or acetic acid (desirably all three) with respect to light condensed liquid phase 30. The second vapor phase stream 36 overhead is deficient with methyl acetate, methanol, and/or acetic acid (desirably all three) with respect to said sidestream 80 and, desirably, also with respect to the higher boiling liquid phase residuum stream 38. Desirably, the second vapor phase stream 36 overhead is enriched with PRC, notably acetaldehyde, with respect to both the sidestream 80 and the higher boiling liquid phase residuum stream 38.

Further in accordance with this second embodiment of the present invention, second vapor phase stream 36 is extracted with water (generally indicated by 70) to remove residual PRC's, notably acetaldehyde. Extraction in accordance with this second embodiment is conducted in accordance with the extraction procedures disclosed for the first embodiment.

Operating in accordance with the first embodiment without a sidestream, the process has been found to achieve the following results respecting the separation capabilities of distillation column 18:

| Component | Weight Percent in Stream 30/32 | Weight Percent in Stream 36 | Weight Percent in Stream 38 |
|---|---|---|---|
| Methyl iodide | 1.5 | 74.5 | <0.1 |
| Methyl acetate | 6.0 | 1.4 | 6.1 |
| Methanol | 4.0 | 0.2 | 4.1 |
| Acetic acid | 15 | <0.1 | 15.3 |
| Water | 73 | 1.6 | 74.5 |
| Acetaldehyde | 0.5 | 22.2 | 0.1 |

Operating in accordance with the second embodiment with a sidestream, it is expected that the following results respecting the separation capabilities of distillation column 18 can be achieved:

| Component | Weight Percent in Stream 30/32 | Weight Percent in Stream 36 | Weight Percent in Stream 38 | Weight Percent in Stream 80 |
|---|---|---|---|---|
| Methyl iodide | 1.5 | 46.8 | <0.1 | 28.7 |
| Methyl acetate | 4.0 | 0.4 | 1.7 | 60.4 |
| Methanol | 1.0 | <0.1 | 1.0 | 0.5 |
| Acetic acid | 15 | <0.1 | 15.7 | 0.5 |
| Water | 78 | 0.8 | 81.6 | 7.4 |
| Acetaldehyde | 0.5 | 52 | <0.1 | 2.5 |

This inventive process has been found to reduce and/or remove PRC's and their precursors, multi-carbon alkyl iodide impurities, and propionic and higher carboxylic acids from the carbonylation process. It has also been shown that acetaldehyde and its derivatives are reduced and/or removed by sufficient amounts such that it is possible to keep the concentration of propionic acid in the acetic acid product below about 500 parts per million by weight, preferably below about 300 parts per million, and most preferably below 250 parts per million.

In variations of the embodiments of the present invention, it is important to inhibit the formation of various aldehyde related polymers and condensation products in distillation column 18. Acetaldehyde polymerizes to form metaldehyde and paraldehyde. These polymers generally are low molecular weight, less than about 200. Higher molecular weight polymers of acetaldehyde can also form. These higher molecular weight polymers (molecular weight greater than about 1000) are believed to form during processing of the light phase and are viscous and thixotropic. Acetaldehyde can also undergo undesirable aldol condensation reactions.

The formation of these impurities, i.e., metaldehyde and paraldehyde and higher molecular weight polymers of acetaldehyde, can be suppressed by introducing into distillation column 18 a flush stream containing at least water and/or acetic acid.

While the invention has been described with reference to the preferred embodiments, obvious modifications and alterations are possible by those skilled in the related art having the benefits of this disclosure. Therefore, it is intended that the invention include all such modifications and alterations to the full extent that they come within the scope of the following claims or the equivalents thereof.

What is claimed is:

1. A process for removing permanganate reducing compounds (PRC's) from a carbonylation product, the process comprising the steps of:

(a) separating the carbonylation product produced by a carbonylation process to provide a first vapor stream comprising acetic acid and a less volatile catalyst phase;
(b) distilling the first vapor stream to yield a first sidestream comprising acetic acid and a second vapor stream comprising methyl iodide, methyl acetate, and at least one PRC;
(c) condensing the second vapor stream and biphasically separating the condensed second vapor stream to form a heavy liquid phase and a light liquid phase;
(d) distilling a portion of the light liquid phase in a single distillation column to form a third vapor stream and a higher boiling liquid phase residuum, wherein the third vapor stream is enriched with PRC's and methyl iodide with respect to the higher boiling liquid phase residuum; and
(e) condensing the third vapor stream and extracting a portion of the condensed third vapor stream with an extractant to obtain an aqueous acetaldehyde stream comprising the at least one PRC and a raffinate comprising methyl iodide.

2. The process of claim 1, further comprising returning a portion of the raffinate to the carbonylation process.

3. The process of claim 1, wherein total concentration of methyl acetate and methanol in the third vapor stream is less than about 10 wt. %.

4. The process of claim 1, wherein total concentration of methyl acetate and methanol in the third vapor stream is less than about 5 wt. %.

5. The process of claim 1, wherein concentration of acetaldehyde in the higher boiling liquid phase residuum is less than about 0.3 wt %.

6. The process of claim 1, wherein the extractant comprises water.

7. The process of claim 1, wherein the portion of the condensed third vapor stream is extracted in the presence of dimethyl ether.

8. The process of claim 7, wherein the dimethyl ether is formed in situ.

9. The process of claim 1, further comprising removing a second sidestream comprising methyl acetate from the single distillation column of step (d), wherein the higher boiling liquid phase residuum and the second sidestream are cumulatively enriched with methyl acetate with respect to said third vapor stream.

10. The process of claim 1, wherein the second vapor stream further comprises methanol, water, acetic acid, and mixtures thereof.

11. The process of claim 1, wherein the first sidestream comprises less than 500 ppm propionic acid.

12. The process of claim 1, wherein the first sidestream comprises less than 300 ppm propionic acid.

13. The process of claim 1, wherein the first sidestream comprises less than 200 ppm propionic acid.

14. The process of claim 1, further comprising feeding a flush stream containing at least water and/or acetic acid to the single distillation column of step (d).

15. The process of claim 1, further comprising distilling a portion of the heavy liquid phase in the single distillation column of step (d).

16. A process for removing permanganate reducing compounds (PRC's) from a carbonylation product, the process comprising the steps of:

(a) separating a portion of the carbonylation product in a light ends column into a first vapor stream comprising methyl acetate, methyl iodide, and at least one PRC, and a first sidestream comprising acetic acid;

(b) separating the first vapor stream into a light liquid phase and a heavy liquid phase;
(c) distilling a portion of the light liquid phase in a single distillation column into a second vapor stream, and a bottoms stream, wherein the second vapor stream is enriched with at least one PRC and methyl iodide, and total concentration of methanol and methyl acetate in the second vapor stream is less than about 10 wt. %; and
(d) condensing the second vapor stream and extracting a portion of the second condensed vapor stream to obtain an aqueous acetaldehyde stream comprising the at least one PRC and a raffinate comprising methyl iodide.

17. The process of claim 16, wherein total concentration of methyl acetate and methanol in the second vapor stream is less than about 5 wt. %.

18. The process of claim 16, wherein concentration of acetaldehyde in the bottoms stream is less than about 0.3 wt %.

19. The process of claim 16, wherein the extractant comprises water.

20. The process of claim 16, wherein the portion of the condensed second vapor stream is extracted in the presence of dimethyl ether.

21. The process of claim 20, wherein the dimethyl ether is formed in situ.

22. The process of claim 16, further comprising removing a second sidestream comprising methyl acetate from the distillation column of step (c), wherein the bottoms stream and the second sidestream are cumulatively enriched with methyl acetate with respect to said second vapor stream.

23. The process of claim 16, wherein the first vapor stream further comprises methanol, water, acetic acid, and mixtures thereof.

24. The process of claim 16, wherein the first sidestream comprises less than 500 ppm propionic acid.

25. The process of claim 16, wherein the first sidestream comprises less than 300 ppm propionic acid.

26. The process of claim 16, wherein the first sidestream comprises less than 200 ppm propionic acid.

27. The process of claim 16, further comprising feeding a flush stream containing at least water and/or acetic acid to the distillation column of step (c).

28. The process of claim 16, further comprising distilling a portion of the heavy liquid phase in the distillation column of step (c).

29. The process of claim 16, wherein the portion of the light liquid phase is distilled in a single a distillation column.

30. The process of claim 1, wherein total concentration of methyl iodide in the higher boiling liquid phase residuum is less than 0.1 wt. %.

31. The process of claim 16, wherein total concentration of methyl iodide in the bottoms stream is less than 0.1 wt. %.

\* \* \* \* \*